(12) United States Patent
Moore, Jr. et al.

(10) Patent No.: US 6,322,822 B1
(45) Date of Patent: *Nov. 27, 2001

(54) BIOCIDAL APPLICATIONS OF CONCENTRATED AQUEOUS BROMINE CHLORIDE SOLUTIONS

(75) Inventors: Robert M. Moore, Jr.; Christopher J. Nalepa, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/404,184

(22) Filed: Sep. 24, 1999

Related U.S. Application Data

(63) Continuation-in-part of application No. 09/088,300, filed on Jun. 1, 1998, now Pat. No. 6,068,861.

(51) Int. Cl.⁷ .......................... A01N 39/00; A01N 59/02; A01N 59/08; A01N 59/00

(52) U.S. Cl. .......................... 424/703; 424/615; 424/663; 424/665; 424/680; 424/723

(58) Field of Search .................. 424/703, 615, 424/663, 665, 680, 723

(56) References Cited

U.S. PATENT DOCUMENTS

| | | | |
|---|---|---|---|
| 3,152,073 | 10/1964 | Morton | 210/62 |
| 3,170,883 | 2/1965 | Owen et al. | 252/187 |
| 3,308,062 | 3/1967 | Gunther | 210/58 |
| 3,328,294 | 6/1967 | Self et al. | 210/62 |
| 3,558,503 | 1/1971 | Goodenough et al. | 252/187 |
| 3,589,859 | 6/1971 | Foroulis et al. | 21/2.7 |
| 3,711,246 | 1/1973 | Foroulis | 21/2.7 |
| 3,749,672 | 7/1973 | Golton et al. | 252/95 |
| 3,767,586 | 10/1973 | Rutkiewic | 252/187 H |
| 4,032,460 | 6/1977 | Zilch et al. | 252/8.55 B |
| 4,237,090 | 12/1980 | DeMonbrun et al. | 162/161 |
| 4,295,932 | 10/1981 | Pocius | 162/161 |
| 4,382,799 | 5/1983 | Davis et al. | 8/107 |
| 4,427,435 | 1/1984 | Lorenz et al. | 71/67 |
| 4,451,376 | 5/1984 | Sharp | 210/701 |
| 4,465,598 | 8/1984 | Darlington et al. | 210/721 |
| 4,476,930 | 10/1984 | Watanabe | 166/279 |
| 4,490,308 | 12/1984 | Fong et al. | 260/513 N |
| 4,539,071 | 9/1985 | Clifford et al. | 162/161 |
| 4,546,156 | 10/1985 | Fong et al. | 526/240 |
| 4,566,973 | 1/1986 | Masler, III et al. | 210/701 |
| 4,595,517 | 6/1986 | Abadi | 252/82 |
| 4,595,691 | 6/1986 | LaMarre et al. | 514/367 |
| 4,604,431 | 8/1986 | Fong et al. | 525/357 |
| 4,642,194 | 2/1987 | Johnson | 210/699 |
| 4,643,835 | 2/1987 | Koeplin-Gall et al. | 210/754 |
| 4,661,503 | 4/1987 | Martin et al. | 514/372 |
| 4,680,339 | 7/1987 | Fong | 525/54.11 |
| 4,680,399 | 7/1987 | Buchardt | 546/139 |
| 4,703,092 | 10/1987 | Fong | 525/351 |
| 4,711,724 | 12/1987 | Johnson | 210/699 |
| 4,752,443 | 6/1988 | Hoots et al. | 422/13 |
| 4,759,852 | 7/1988 | Trulear | 210/699 |
| 4,762,894 | 8/1988 | Fong et al. | 525/344 |
| 4,777,219 | 10/1988 | Fong | 525/329.4 |
| 4,801,388 | 1/1989 | Fong et al. | 210/701 |
| 4,802,990 | 2/1989 | Inskeep, Jr. | 210/699 |
| 4,822,513 | * 4/1989 | Corby | 252/106 |
| 4,846,979 | 7/1989 | Hamilton | 210/754 |
| 4,883,600 | 11/1989 | MacDonald et al. | 210/696 |
| 4,886,915 | 12/1989 | Favstritsky | 564/503 |
| 4,898,686 | 2/1990 | Johnson et al. | 252/389.2 |
| 4,906,651 | 3/1990 | Hsu | 514/372 |
| 4,923,634 | 5/1990 | Hoots et al. | 252/389.2 |
| 4,929,424 | 5/1990 | Meier et al. | 422/9 |
| 4,929,425 | 5/1990 | Hoots et al. | 422/13 |
| 4,966,716 | 10/1990 | Favstristsky et al. | 210/755 |
| 4,992,209 | 2/1991 | Smyk et al. | 252/387 |
| 4,995,987 | 2/1991 | Whitekettle et al. | 210/754 |
| 5,034,155 | 7/1991 | Soeder et al. | 252/389.23 |
| 5,035,806 | 7/1991 | Fong et al. | 210/701 |

(List continued on next page.)

FOREIGN PATENT DOCUMENTS

| | | |
|---|---|---|
| 9015780 | 12/1990 | (WO) . |
| 9720546 | 6/1997 | (WO) . |
| 9720909 | 6/1997 | (WO) . |
| 9734827 | 9/1997 | (WO) . |
| 9743392 | 11/1997 | (WO) . |
| 9815609 | 4/1998 | (WO) . |
| 9906320 | 2/1999 | (WO) . |
| 9932596 | 7/1999 | (WO) . |

OTHER PUBLICATIONS

Ault, et al., "Infrared and Raman Spectra of the M+Cl3–Ion Pairs and Their Chlorine–Bromine Counterparts in Argon Matrices", The Journal of Chemical Physics, vol. 65, No. 12, Jun. 15, 1976, pp. 4853–4859.

Primary Examiner—Jose' G. Dees
Assistant Examiner—A Hon Pryor
(74) Attorney, Agent, or Firm—E. E. Spielman, Jr.

(57) ABSTRACT

Methods for disinfecting surfaces and for sanitizing bodies of water using a single-feed, bromine-based biocide are described. These methods use concentrated liquid biocide compositions comprising biocidally active bromine as the biocide. Also described is a process of producing the concentrated liquid biocide composition: mixed together are (a) bromine chloride and (b) an aqueous solution of alkali metal salt of sulfamic acid having a pH of at least about 7, in amounts such that (i) the active bromine content of the composition is at least about 100,000 ppm (wt/wt), and (ii) the atom ratio of nitrogen to active bromine in the composition is greater than 0.93. Use of bromine chloride as the source of the active bromine in the process is advantageous because in the resulting aqueous compositions, all of the bromine of the bromine chloride is made available as active bromine in solution. In other words, the chlorine of the bromine chloride is converted in the process to dissolved alkali metal chloride salt, thereby liberating all of the bromine as the active bromine content of the biocidal composition.

50 Claims, No Drawings

U.S. PATENT DOCUMENTS

| | | | |
|---|---|---|---|
| 5,047,164 | 9/1991 | Corby | 252/106 |
| 5,055,285 | 10/1991 | Duncan et al. | 423/473 |
| 5,118,426 | 6/1992 | Duncan et al. | 210/721 |
| 5,120,452 | 6/1992 | Ness et al. | 210/754 |
| 5,120,797 | 6/1992 | Fong et al. | 525/329.4 |
| 5,141,652 | 8/1992 | Moore, Jr. et al. | 210/754 |
| 5,179,173 | 1/1993 | Fong et al. | 525/329.4 |
| 5,192,459 | 3/1993 | Tell et al. | 252/106 |
| 5,194,238 | 3/1993 | Duncan et al. | 423/473 |
| 5,196,126 | 3/1993 | O'Dowd | 210/754 |
| 5,202,047 | 4/1993 | Corby | 252/106 |
| 5,259,985 | 11/1993 | Nakanishi et al. | 252/180 |
| 5,264,136 | 11/1993 | Howarth et al. | 210/754 |
| 5,389,384 | 2/1995 | Jooste | 424/661 |
| 5,414,652 | 5/1995 | Mieda et al. | 365/122 |
| 5,424,032 | 6/1995 | Christensen et al. | 422/14 |
| 5,443,849 | 8/1995 | Corby | 424/667 |
| 5,464,636 | 11/1995 | Hight et al. | 424/661 |
| 5,525,241 | 6/1996 | Clavin et al. | 210/753 |
| 5,527,547 | 6/1996 | Hight et al. | 424/661 |
| 5,589,106 | 12/1996 | Shim et al. | 252/387 |
| 5,607,619 | 3/1997 | Dadgar et al. | 252/187.2 |
| 5,679,239 | 10/1997 | Blum et al. | 205/556 |
| 5,683,654 * | 11/1997 | Dallmier | 422/482 |
| 5,795,487 | 8/1998 | Dallmier | 210/754 |
| 5,922,745 | 7/1999 | McCarthy et al. | 514/372 |
| 5,942,126 | 8/1999 | Dallmier et al. | 210/756 |
| 6,007,726 | 12/1999 | Yang et al. | 210/752 |
| 6,068,861 | 5/2000 | Moore, Jr et al. | 424/703 |
| 6,123,870 | 9/2000 | Yang et al. | 252/186.1 |

\* cited by examiner

BIOCIDAL APPLICATIONS OF CONCENTRATED AQUEOUS BROMINE CHLORIDE SOLUTIONS

REFERENCE TO RELATED APPLICATIONS

This application is a continuation-in-part of commonly-owned U.S. application Ser. No. 09/088,300, filed Jun. 1, 1998, now U.S. Pat. No. 6,068,861, which issued from Application (CPA) No. 09/088,300.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine-based biocides into a water system is through the use of aqueous NaBr in conjunction with NaOCl bleach. The user feeds both materials to a common point whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on site just prior to its introduction to the water. Furthermore, the feeding and metering of two liquids is cumbersome, especially as the system has to be designed to allow time for the activation of bromide ion to occur. Consequently many biocide users have expressed the need for a single-feed, bromine-based biocide. Molecular bromine chloride has been considered to meet these demands. It is a liquid at room temperature and can be fed directly to the water system, where immediate hydrolysis occurs to yield HOBr.

$$BrCl+H_2O \rightarrow HOBr+HCl \qquad (1)$$

Properties of bromine chloride are listed in Table 1.

TABLE 1

| Property | Bromine Chloride (BrCl) |
| --- | --- |
| Appearance | Fuming, red liquid or gas |
| Boiling Point | 5° C. |
| Vapor Pressure (25° C.) | 1800 mm |
| Corrosivity | Corrodes most metals in the presence of water |

It can be seen that certain characteristics of this material—especially its corrosiveness, high vapor pressure and fuming tendency—necessitate care and skill in its handling and use.

Early efforts to provide a single-feed, bromine-based biocide comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of biocidally active bromine to a water system using a single feed. As in the case of bromine chloride, the ethanolammonium hydrogen perbromide hydrolyzed in water to release HOBr. The vapor pressures of these solutions were lower than bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water, and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine-based biocides such as BrClDMH (1,3-bromochloro-5,5-dimethylhydantoin) are limited in the amount of material that can be dissolved in water and fed as a liquid to the water treatment system. For example, the solubility of BrClDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypobromite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

Thus, there remains a need for methods of disinfecting surfaces and of sanitizing bodies of water using a single-feed, bromine-based biocide that is water-soluble, non-acidic, and noncorrosive.

THE INVENTION

This invention provides methods for disinfecting surfaces and for sanitizing bodies of water using a single-feed, bromine-based biocide. Examples of surfaces that may be disinfected using the methods of this invention include kitchen counters, bathroom counters, walls, and floors. The bodies of water that may be sanitized using the methods of this invention include cooling water systems, waste water effluents, pulp and paper mills, oilfields, air washers, fire reservoirs, and evaporative condensers. These methods use concentrated liquid biocide compositions comprising biocidally active bromine as the single-feed, bromine-based biocide. This invention further involves a process of forming aqueous solutions of bromine chloride, and in so doing, provides novel and eminently useful concentrated solutions of biocidally active bromine. These solutions of bromine chloride perform as well as bleach towards planktonic (solution) bacteria. Further, these solutions of bromine chloride are more effective than bleach versus biofilm (surface) bacteria, which are more difficult to kill than planktonic bacteria.

In one embodiment of this invention, a method for disinfecting a surface is provided. This method comprises applying to the surface a concentrated liquid biocide composition comprised of (a) bromine chloride and (b) an aqueous solution of alkali metal salt of sulfamic acid having a pH of at least about 7. The amounts of (a) and (b) are such that (i) the active bromine content of the composition is at least about 100,000 ppm (wt/wt), and (ii) the atom ratio of nitrogen to active bromine in the composition is greater than 0.93.

Another embodiment of this invention provides a method of sanitizing a body of water which method comprises introducing into the body of water a concentrated liquid biocide composition. The biocidal composition is comprised of (a) bromine chloride and (b) an aqueous solution of alkali metal salt of sulfamic acid having a pH of at least about 7. The amounts of (a) and (b) are such that, in the biocidal composition, (i) the active bromine content is at least about 100,000 ppm (wt/wt), and (ii) the atom ratio of nitrogen to active bromine is greater than 0.93.

Still another embodiment of this invention provides a method for disinfecting a surface. This method comprises applying to the surface a concentrated liquid biocide composition comprised of (a) alkali metal dichlorohypobromite and (b) an aqueous solution of alkali metal salt of sulfamic acid having a pH of at least about 7. The amounts of (a) and (b) are such that (i) the active bromine content of the composition is at least about 100,000 ppm (wt/wt), and (ii) the atom ratio of nitrogen to active bromine in the composition is greater than 1.

Yet another embodiment of this invention provides a method of sanitizing a body of water which comprises introducing into the body of water a concentrated liquid biocide composition. The biocidal composition is comprised of (a) alkali metal dichlorohypobromite and (b) an aqueous solution of alkali metal salt of sulfamic acid having a pH of at least about 7. The amounts of (a) and (b) are such that, in the biocidal composition, (i) the active bromine content is at least about 100,000 ppm (wt/wt), and (ii) the atom ratio of nitrogen to active bromine is greater than 1.

The above and other embodiments of this invention will be still further apparent from the ensuing description and appended claims.

An advantage of this invention is that the concentrated liquid biocide compositions provided herein are at least as effective as bleach as a biocide, without the undesirable properties of bleach, which include instability and an unpleasant odor. Thus, the methods of this invention may replace those which use bleach in biocidal applications. The organisms that may be controlled using the methods of this invention include bacteria, fungi, slime, and mollusks. Another advantage of the methods of this invention is that the concentrated liquid biocide compositions provided herein are water-soluble, non-acidic, and noncorrosive. A further advantage of this invention is that the concentrated liquid biocide compositions provided by this invention are single-feed biocides, the term single-feed signifying that the end user need not do any further mixing of components to produce the concentrated liquid biocide composition.

The method for disinfecting a surface comprises applying a concentrated liquid biocide composition of bromine chloride or alkali metal dichlorohypobromite to the surface to be disinfected. The concentrated liquid biocide composition may be applied to the surface to be disinfected in various ways. The composition may be poured directly onto the surface, sprayed onto the surface, or poured or sprayed onto an applicator which is then brought into contact with the surface. Applicators include, but are not limited to, cloths, sponges, paper towels, and mops.

The method of sanitizing a body of water comprises introducing a concentrated liquid biocide composition of bromine chloride or alkali metal dichlorohypobromite into the body of water. A variety of methods may be used to introduce the concentrated liquid biocide composition to the body of water to be sanitized. The concentrated liquid biocide composition may be added directly to the body of water, either all at once or slowly over time, for example via a pump or feeder. In systems in which the water is circulated through an apparatus, the concentrated liquid biocide composition may be added to this apparatus.

The addition of the concentrated liquid biocide composition to the body of water to be sanitized preferably yields a concentration of biocide in the body of water such that in the range of from about 2 to about 10 milligrams per liter of total available halogen, expressed as $Cl_2$, is present in the body of water. In a preferred embodiment, the concentrated liquid biocide composition is introduced into the body of water as required, such that in the range of from about 2 to about 10 milligrams per liter of total available halogen, expressed as $Cl_2$, is maintained within the body of water. A more preferred amount of total available halogen, expressed as $Cl_2$, in the body of water is from about 2 to about 5 milligrams per liter. These concentrations of total available halogen, expressed as $Cl_2$, are known in the art to be sufficient for sanitizing a body of water and for maintaining sanitization of a body of water.

This invention provides a process of producing a concentrated liquid biocide composition which comprises mixing (a) bromine chloride with (b) an aqueous solution of alkali metal salt of sulfamic acid (preferably the sodium salt), the solution having a pH of at least about 7, and preferably in the range of 7 to about 13.5. The amounts of (a) and (b) used are such that (i) the content of active bromine in the composition is at least 100,000 ppm (wt/wt), and (ii) the atom ratio of nitrogen to active bromine in the composition is greater than 0.93. It is preferred to utilize an atom ratio of nitrogen to active bromine that is greater than 1, and the pH is preferably in the range of 7 to about 13.5.

In a preferred process for producing the concentrated liquid biocide composition, the aqueous solution of alkali metal salt of sulfamic acid used in the process is preformed by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7. If sulfamic acid itself is used as the starting material, it is used initially as a slurry in water with which the alkali metal base is mixed. It is preferred that the alkali metal salt of sulfamic acid is the lithium, sodium, or potassium salt; more preferred are the sodium and potassium salts. Highly preferred as the alkali metal salt of sulfamic acid is the sodium salt.

When mixing the bromine chloride with the aqueous solution of alkali metal salt of sulfamic acid, it is desirable to maintain the desired pH of the resulting solution at 7 or above by also introducing into the solution (continuously or intermittently, as desired) additional alkali metal base, such as by a co-feed of an aqueous solution of alkali metal base.

The use of bromine chloride as the source of the active bromine in the above process is advantageous because in the resulting aqueous compositions, all of the bromine of the bromine chloride is made available as active bromine in solution. In other words, the chlorine of the bromine chloride is converted in the process to dissolved alkali metal chloride salt, thereby liberating the bromine as the active bromine content of the biocidal composition. Thus the more expensive component of the bromine chloride—viz., bromine—is fully utilized in forming active bromine in the aqueous biocidal composition, and concurrently the less expensive component—the anionic chlorine in the bromine chloride—makes this beneficial result possible.

By utilizing bromine chloride with caustic in the composition, higher levels of active halogen are achievable compared to the levels obtained by the addition of sodium hypochlorite to sodium bromide. The process and the compositions formed also have about twice the content of active bromine as the most concentrated solutions produced pursuant to the Goodenough, et al. patent. Moreover, even at the high levels of active bromine that exist in the compositions used in this invention, it has been found possible to provide biocidal compositions that maintain these high levels of active bromine for at least a two month period, and that do not exhibit a visible or offensive vapor or odor during this period.

This invention also provides an aqueous biocide composition comprising water having in solution therein (i) an active bromine content derived from bromine chloride of at least about 100,000 ppm (wt/wt), (ii) an alkali metal salt of sulfamic acid, and (iii) an alkali metal chloride, wherein the relative proportions of (i) and (ii) are such that the atom ratio of nitrogen to active bromine in the resultant composition is greater than 1, and the pH of the composition is at least 7, and preferably in the range of 7 to about 13.5. Again, the preferred alkali metal salt of sulfamic acid is the lithium, sodium, or potassium salt; more preferably, it is the sodium or potassium salt; the most preferred alkali metal salt of sulfamic acid is the sodium salt. Similarly, the alkali metal chloride is preferably lithium chloride, sodium chloride, or potassium chloride; more preferably it is sodium chloride or potassium chloride. Highly preferred as the alkali metal chloride is sodium chloride. In a less preferred embodiment, (iii) is an alkali metal bromide, most preferably sodium bromide.

This invention further provides a process for producing alkali metal dichlorohypobromite, $M[BrCl_2]$ (M=alkali metal), which is preformed by pre-mixing bromine chloride with aqueous alkali metal chloride, and the bromine chloride is used in this form to provide the active bromine content of the biocidal composition. The alkali metal of the alkali metal dichlorohypobromite may be lithium, sodium, potassium, rubidium, or cesium; preferred are lithium, sodium, and potassium; more preferred are sodium and potassium. Sodium dichlorohypobromite is the most preferred alkali metal dichlorohypobromite. Dichlorohypobromite is also referred to in the art as dichlorobromate, bromide dichloride, and dichlorobromide.

To form the biocidal composition, the alkali metal dichlorohypobromite is mixed with an aqueous solution of an alkali metal salt of sulfamic acid which has a pH of at least 7. In the resultant biocidal composition, the atom ratio of nitrogen to active bromine is greater than 0.93. It is preferred that the atom ratio is greater than 1.

In each of the embodiments of this invention, the atom ratio of nitrogen to active bromine in the biocidal composition is preferably in the range of about 1.1 to about 1.5. Still higher ratios can be employed, if desired.

The following examples are presented for purposes of illustration, and are not intended to impose limitations on the scope of this invention.

EXAMPLES

A general procedure for preparing the compositions of this invention using sulfamic acid involves, as a first step, forming a slurry of sulfamic acid in water. Typically the pH of this slurry is below 1 pH unit. Sodium hydroxide at 50% concentration is then added until the solid is completely dissolved. Additional 50% NaOH is added until the desired pH is reached. Bromine chloride is then added at a rate to allow dissolution without forming a pool of halogen on the bottom of the reactor. On a laboratory scale, a convenient rate of addition is approximately two drops per second. Sodium hydroxide (e.g., 25% or 50%) is co-fed to the reactor to maintain the desired pH (e.g., in the range of 7 to about 13.5, and it may be possible to operate even at a pH in the range of 13.5 to 14). It has been found that stable solutions containing as much as 26% active bromine (11.5% on an active chlorine basis) can be prepared by the process of this invention.

Various compositions were prepared using the above general procedure and the active bromine content of the resultant compositions was determined analytically. The conditions used and results obtained (observations on odor and vapor, and initial contents of active bromine in the solutions) are summarized in Table 2.

TABLE 2

Data on Prepared Sulfamic Acid Bromine Chloride Solutions

| Ex. No. | Halogen | pH | $SA_{eq}$ | Odor and Vapor Comments | Active $Br_2$, wt %* |
|---|---|---|---|---|---|
| 1** | BrCl | 7 | 0.92 | Strong Br odor, slight fuming | 11.2% |
| 2 | BrCl | 12.5 | 0.94 | Slight sweet smell, no observed vapor | 18.0% |
| 3 | BrCl | 12.8 | 1.41 | Slight sweet smell, no observed vapor | 17.6% |
| 4 | BrCl | 13.5 | 1.35 | | 16.2% |

$SA_{eq}$ = Sulfamic acid to halogen mole ratio.
*Determined by titration using starch-iodine-sodium arsenite method.
**Comparative example The specific details for Examples 1–4 of Table 2 are given below. Example 5 illustrates the embodiment of the invention wherein an alkali metal dichlorohypobromite is utilized as the source of active bromine. Examples 6 and 7 illustrate the efficacy of bromine chloride towards bacteria.

Example 1
Bromine Chloride, Caustic and Sodium Sulfamate at Neutral pH

A 1 liter flask was charged with 52.0 g of sulfamic acid and 250 g of water. Sodium sulfamate was prepared by adding 60.0 g of 50% sodium hydroxide to the stirred slurry. Bromine chloride was prepared by adding 20 g of chlorine to 47.0 g of bromine. This bromine chloride was then co-fed with 210 g of 25% sodium hydroxide to maintain the pH between 6 and 8.5 mL of 1 M hydrochloric acid were added to bring the final pH to approximately 7±0.5. The solution, which contained some solids, was transferred to an amber bottle for storage. Starch-iodine titration of a sample of the solution indicated that it had an active bromine concentration of 11.2%.

Example 2
Bromine Chloride, Caustic and Sodium Sulfamate

A 1 liter flask was charged with 107 g of sulfamic acid and 200 g of water. Sodium sulfamate was prepared by adding 93.9 g of 50% sodium hydroxide to the stirred slurry. Bromine chloride was prepared by adding 39 g of chlorine to 96.0 g of bromine. This bromine chloride was the co-fed with 319 g of 50% sodium hydroxide to maintain the pH between 11 and 13. After stirring for an additional 30 minutes, the solution, which contained some solids, was transferred to an amber bottle for storage. Starch-iodine titration of a sample of the solution indicated that it had an active bromine concentration of 18.0%. Analysis of the solution after three weeks at ambient temperature indicated that the solution still contained more than 90% of its active bromine content.

Example 3
Bromine Chloride, Caustic and Sodium Sulfamate; Larger Scale

A 5 liter flask was charged with 470 g of sulfamic acid and 900 g of water. Sodium sulfamate was prepared by adding 436 g of 50% sodium hydroxide to the stirred slurry. Bromine chloride was prepared by adding 120 g of chlorine to 276 g of bromine. This bromine chloride was then co-fed with 1723 g of 50% sodium hydroxide to maintain the pH between 12 and 13. After stirring for an additional 60 minutes, the orange, clear solution was transferred to an polyethylene bottle for storage. Starch-iodine titration of a sample of the solution indicated that it had an active bromine concentration of 17.6%.

Example 4
Bromine Chloride, Caustic and Sodium Sulfamate

A 5 liter flask was charged with 390 g of sulfamic acid and 400 g of water. Sodium sulfamate was prepared by adding 1820 g of 25% sodium hydroxide to the stirred slurry while cooling to keep the temperature below 30° C. 344 g of bromine chloride was then added. The orange, clear solution had a pH of 13.5, and was filtered and transferred to a polyethylene bottle for storage. Starch-iodine titration of a sample of the solution indicated that it had an active bromine concentration of 16.2%.

Example 5
Reducing Vapor Pressure of Sodium Dichlorohypobromite with Sodium Sulfamate Sodium dichlorohypobromite, Na[$BrCl_2$], is prepared by adding 30.6 g of bromine chloride to 154 g of 3M aqueous sodium chloride. Sodium sulfamate was prepared by slurrying 24.3 g of sulfamic acid in 9 g of water and adding 24.0 g of 50% sodium hydroxide dropwise to the sulfamic acid slurry; the flask heated noticeably and the solid dissolved. This sodium sulfamate solution was dropped into the 184.6 g of sodium dichlorohypobromite. An additional 24 g of 50% sodium hydroxide was added to raise the pH to 7. Analysis of this solution indicated that it had an active bromine concentration of 12.0%.

Example 6
Efficacy of BrCl/Sodium Sulfamate Solutions Versus Biofilm (surface) Bacteria Biocide Solutions Synthetic water is prepared by adding 0.22 g $CaCl_2$, 0.168 g $NaHCO_3$, and 0.014 g NaCl to 1 L of deionized, distilled water. The mixture is sterilized by filtration through a 0.2 $\mu$m filter. This solution affords water containing 200 ppm calcium hardness (as $CaCO_3$), 150 ppm of alkalinity (as $CaCO_3$), and 150 ppm of chloride, and which has a pH of 8.05.

The stock hypochlorous acid solution is prepared from sodium hypochlorite solution (0.41 g, >4%, actual ~2.7%) diluted to 100 g with synthetic water. The solution is stored in a 4 oz. amber glass bottle in the refrigerator. Stock hypobromous acid is blended from sodium hypochlorite (0.42 g, 0.15 mmol) and sodium bromide (0.028 g, 0.27 mmol); this solution is also stored in a 4 oz. amber glass bottle in the refrigerator. 0.0054 g of BrClDMH, 0.0054 g of $Br_2DMH$, and 0.0033 g of trichloroisocyanuric acid are each added with stirring to separate 20 g solutions of synthetic water. The stock BrCl solution is prepared by diluting 0.032 g of the solution from Example 4 with 20 g of synthetic water.

The stock solutions of hypobromous acid (HOBr) and 1,3-bromochloro-5,5-dimethylhydantoin (BrClDMH) were diluted 1:10 for minimum biofilm eradication concentration (MBEC) testing (see below). The stock solutions of BrCl, hypochlorous acid (HOCl), 1,3-dibromo-5,5-dimethylhydantoin ($Br_2DMH$), and trichloroisocyanuric acid were diluted 1:10 and again 1:2.5 for MBEC testing. The solutions are characterized by performing another 1:10 dilution and analyzing for free or total chlorine by the DPD method using a Hach DR 700 spectrophotometer. The actual oxidant levels in the stock solutions prior to their dilution for the MBEC tests are shown in Table 3.

TABLE 3

| Oxidant Levels in Solutions for Example 6 | | | | | | |
|---|---|---|---|---|---|---|
| Example | 6a | 6a | 6b | 6b | 6c | 6c |
| | Free $Cl_2$ | Total $Cl_2$ | Free $Cl_2$ | Total $Cl_2$ | Free $Cl_2$ | Total $Cl_2$ |
| BrCl | | 20.0 | | 37 ppm | | — |
| HOBr | | 10.0 | | 10.1 ppm | | 10.1 |
| HOCl | 10.1 | | 42 ppm | | 10.4 | |
| $Br_2DMH^a$ | | 10.9 | | 40 ppm | | 9.4 |
| BrClDMH[b] | | 9.8 | | 9.1 ppm | | 9.1 |
| $Cl_3$isocyanuric acid[c] | 10.6 | | 44 ppm | | 10.6 | |

[a]$Br_2DMH$ = 1,3-dibromo-5,5-dimethylhydantoin
[b]BrClDMH = 1,3-bromochloro-5,5-dimethylhydantoin
[c]$Cl_3$isocyanuric acid = trichloroisocyanuric acid Biofilm Preparation

*Pseudomonas aeruginosa* (ATCC 15442) biofilms, *Klebsiella pneumoniae* (University of Calgary Biofilm Research Group, environmental isolate) biofilms, and mixed biofilms are prepared on the pegs of a plate by aerobic incubation in a simple salts medium with 0.1% glucose (24 hours, 35° C.) containing about $5 \times 10^6$ cfu/mL bacterial inoculum. The mixed biofilms of *Pseudomonas aeruginosa* and *Klebsiella pneumoniae* are prepared by inoculating 25 mL media with approximately equal amounts of each organism ($5 \times 10^6$ cfu/mL). The 7-day biofilms are prepared by a slight modification of these procedures: each day, spent media was replaced with fresh media and inocula.

Minimum Biofilm Eradication Concentration

The minimum biofilm eradication concentration (MBEC) is defined as the minimum concentration of agent which results in complete biofilm deactivation. The MBEC technique generally consists of growing identical 24-hour biofilms and then challenging the biofilms with decreasing concentrations of selected antibiotics and/or biocides. After a challenge time, the biofilms are placed in wells of growth media and ultra-sonicated to remove any surviving organisms. After incubating overnight, the wells are checked for turbidity. Clear, transparent wells indicate complete deactivation of biofilm bacteria. Conversely, turbidity (growth) indicates incomplete deactivation.

In all cases, the pegs are then rinsed in synthetic water and challenged by the biocide. Following the biocide challenge, the pegs are rinsed twice with synthetic water and then sonicated into Mueller-Hinton broth (225 μL per well). The broth is then incubated for 18 hours at 35° C. MBEC endpoints were unambiguously determined by absorbance at 650 nm. An absorbance >0.100 was considered a positive indication of growth.

Procedure

Both a 24-hour and a 7-day biofilm are prepared from *P. aeruginosa* (Examples 6a and 6b). A 24-hour biofilm is prepared from equal populations of *P. aeruginosa* and *K. pneumoniae* (Example 6c ). These biofilms are then challenged with several oxidizing biocides. The 7-day biofilms were more difficult to eradicate than the 24-hour biofilms.

All of the MBEC determinations performed in Example 6 used a pH of 8.0 and a one hour challenge time for the MBEC determination. The results of the minimum biofilm eradication concentration (MBEC) determinations are shown in Table 4.

TABLE 4

MBEC Results for Biofilm Bacteria

| | Ex. # | | |
|---|---|---|---|
| | 6a | 6b | 6c |
| | | Bacteria | |
| | *P. aeruginosa* | *P. aeruginosa* | *P. aeruginosa* and *K. pneumoniae* |
| film growth time | 24 hours | 7 days | 24 hours |
| | MBEC | MBEC | MBEC |
| BrCl | 3.8 ppm | 4.6 ppm | not tested |
| HOBr | 2.5 ppm | 7.6 ppm | 2.5 ppm |
| HOCl | 3.8 ppm | 21 ppm | 2.6 ppm |
| $Br_2DMH^a$ | 1.4 ppm | 5 ppm | 2.4 ppm |
| $BrClDMH^b$ | 2.4 ppm | 6.8 ppm | 2.3 ppm |
| $Cl_3$isocyanuric acid$^c$ | 2.0 ppm | 22 ppm | 2.6 ppm |

$^a$$Br_2$DMH = 1,3-dibromo-5,5-diniethylhydantoin
$^b$BrClDMH = 1,3-bromochloro-5,5-dimethylhydantoin
$^c$$Cl_3$isocyanuric acid = trichloroisocyanuric acid Example 7
Efficacy of BrCl/Sodium Sulfamate Solutions Versus Planktonic (solution) Bacteria Biocide Solutions The sodium hypochlorite (NaOCl) solution is an aqueous solution with 5.25% available chlorine. The stock BrCl solution is prepared as in Example 4. Both the NaOCl solution and the BrCl solutions are diluted in a two fold series of dilutions in phosphate buffer at the desired pH for the minimum inhibitory concentration (MIC) tests (see below).

Bacterial Cultures

Cultures of *E. coli*, *P. aeruginosa*, and *S. aureus* are prepared by growing 24-hour cultures of the respective bacteria.

Minimum Inhibitory Concentration

The minimum inhibitory concentration (MIC) is defined as the highest dilution (lowest concentration) which shows complete deactivation of the bacteria. The MIC technique generally consists of growing identical 24-hour bacteria cultures and then challenging a portion of the culture with selected antibiotics and/or biocides. After a challenge time, the challenged portions of the cultures are placed in wells of growth media, and, after incubating overnight, the wells are checked for turbidity. Clear, transparent wells indicate complete deactivation of the bacteria. Conversely, turbidity (growth) indicates incomplete deactivation.

A 0.5 McFarland suspension from a culture is made for minimum inhibitory concentration (MIC) testing. After the challenge time, a 10 μL aliquot is removed to Letheen broth containing 0. 1% sodium thiosulfate. The mixture is incubated at 35° C. for 48 hours.

Procedure

The suspensions from the cultures are each challenged separately with NaOCl and BrCl solutions at pH 7 (Examples 7a–c), and with BrCl solutions at pH 8.5 (Examples 7d–7f). 9.9 mL portions of the twofold-diluted biocide solutions were inoculated with 100 μl of a 0.5 MacFarland suspension of a 24-hour culture. After the challenge time, a 10 μL aliquot is removed to Letheen broth containing 0.1% sodium thiosulfate. The mixture is incubated at 35° C. for 48 hours.

All of the determinations performed in Example 7 used a ten minute challenge time for the MIC determination. The results of the minimum inhibitory concentration (MIC) determinations are shown in Table 5.

TABLE 5

MIC Results for Planktonic Bacteria

| Ex. # | 7a | 7b | 7c | 7d | 7e | 7f |
|---|---|---|---|---|---|---|
| Bacteria | *E. Coli* | *P. aeruginosa* | *S. aureus* | *E. coli* | *P. aeruginosa* | *S. aureus* |
| pH | 7 | 7 | 7 | 8.5 | 8.5 | 8.5 |
| | MIC | MIC | MIC | MIC | MIC | MIC |
| 11 wt % BrCl | 16 ppm | 16 ppm | 16 ppm | 8 ppm | 16 ppm | 16 ppm |
| 5 wt % NaOCl | 8 ppm | 16 ppm | — | — | — | — |

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method for disinfecting a surface which comprises applying to said surface a concentrated liquid biocide composition formed from (a) bromine chloride and (b) an aqueous solution of alkali metal salt of sulfamic acid and alkali metal base, said solution having a pH of at least about 7, in amounts such that (i) the active bromine content of said composition is at least about 100,000 ppm (wt/wt), (ii) the atom ratio of nitrogen to active bromine in said composition is greater than 0.93, and (iii) said composition has a pH of at least 7.

2. A method according to claim 1 wherein said concentrated liquid biocide composition is applied to said surface by pouring said concentrated liquid biocide composition onto said surface.

3. A method according to claim 1 wherein said concentrated liquid biocide composition is applied to said surface by spraying said concentrated liquid biocide composition onto said surface.

4. A method according to claim 1 wherein said concentrated liquid biocide composition is applied to said surface with an applicator.

5. A method according to claim 1 wherein said atom ratio is greater than 1.

6. A method according to claim 1 wherein said aqueous solution of alkali metal salt of sulfamic acid is an aqueous solution of the sodium salt of sulfamic acid.

7. A method according to claim 1 wherein said aqueous solution of alkali metal salt of sulfamic acid is formed by mixing together in water (i) sulfamic acid and/or an alkali metal salt of sulfamic acid, and (ii) alkali metal base in proportions such that an aqueous solution of alkali metal salt of sulfamic acid is formed having a pH of at least 7.

8. A method according to claim 7 wherein said alkali metal base is a sodium base such that said aqueous solution of alkali metal salt of sulfamic acid is an aqueous solution of the sodium salt of sulfamic acid.

9. A method according to claim 7 wherein, at the time (i) and (ii) are mixed together, the alkali metal base is in the form of a preformed aqueous solution of alkali metal base, and (i) is sulfamic acid in the form of a preformed slurry of sulfamic acid in water.

10. A method according to claim 1 wherein the concentrated liquid biocide composition further comprises an alkali metal chloride.

11. A method according to claim 10 wherein the alkali metal is sodium.

12. A method according to claim 1 wherein the concentrated liquid biocide composition further comprises an alkali metal bromide.

13. A method according to claim 12 wherein the alkali metal is sodium.

14. A method according to claim 1 wherein the pH of said composition is in the range of from 7 to about 13.5.

15. A method of sanitizing a body of water which comprises introducing into said body of water a concentrated liquid biocide composition formed from (a) bromine chloride and (b) an aqueous solution of alkali metal salt of sulfamic acid and alkali metal base, said solution having a pH of at least about 7, such that (i) the active bromine content of said composition is at least about 100,000 ppm (wt/wt), (ii) the atom ratio of nitrogen to active bromine in said composition is greater than 0.93, and (iii) said composition has a pH of at least 7.

16. A method according to claim 15 wherein said concentrated liquid biocide composition is introduced directly into said body of water.

17. A method according to claim 15 wherein said concentrated liquid biocide composition is introduced into said body of water slowly over time.

18. A method according to claim 15 wherein said concentrated liquid biocide composition is introduced into said body of water via an apparatus through which the water is circulated.

19. A method according to claim 15 wherein the addition of said concentrated liquid biocide composition to said body of water yields in the range of from about 2 to about 10 milligrams per liter of total available halogen, expressed as $Cl_2$.

20. A method according to claim 19 wherein the total available halogen, expressed as $Cl_2$, is in the range of from about 2 to about 5 milligrams per liter.

21. A method according to claim 15 wherein the concentrated liquid biocide composition is introduced into said body of water as required, such that in the range of from about 2 to about 10 milligrams per liter of total available halogen, expressed as $Cl_2$, is maintained within said body of water.

22. A method according to claim 21 wherein the total available halogen, expressed as $Cl_2$, is in the range of from about 2 to about 5 milligrams per liter.

23. A method according to claim 15 wherein said atom ratio is greater than 1.

24. A method according to claim 15 wherein said aqueous solution of alkali metal salt of sulfamic acid is an aqueous solution of the sodium salt of sulfamic acid.

25. A method according to claim 15 wherein said aqueous solution of alkali metal salt of sulfamic acid is formed by mixing together in water (i) sulfamic acid and/or an alkali metal salt of sulfamic acid, and (ii) alkali metal base in proportions such that an aqueous solution of alkali metal salt of sulfamic acid is formed having a pH of at least 7.

26. A method according to claim 25 wherein said alkali metal base is a sodium base such that said aqueous solution of alkali metal salt of sulfamic acid is an aqueous solution of the sodium salt of sulfamic acid.

27. A method according to claim 25 wherein, at the time (i) and (ii) are mixed together, the alkali metal base is in the form of a preformed aqueous solution of alkali metal base, and (i) is sulfamic acid in the form of a preformed slurry of sulfamic acid in water.

28. A method according to claim 15 wherein the concentrated liquid biocide composition further comprises an alkali metal chloride.

29. A method according to claim 28 wherein the alkali metal is sodium.

30. A method according to claim 15 wherein the concentrated liquid biocide composition further comprises an alkali metal bromide.

31. A method according to claim 30 wherein the alkali metal is sodium.

32. A method according to claim 15 wherein the pH of said composition is in the range of from 7 to about 13.5.

33. A method for disinfecting a surface which comprises applying to said surface a concentrated liquid biocide composition formed from (a) alkali metal dichlorohypobromite and (b) an aqueous solution of alkali metal salt of sulfamic acid and alkali metal base, said solution having a pH of at least about 7, in amounts such that (i) the active bromine content of said composition is at least about 100,000 ppm (wt/wt), (ii) the atom ratio of nitrogen to active bromine in said composition is greater than 1, and (iii) said composition has a pH of at least 7.

34. A method according to claim 33 wherein said concentrated liquid biocide composition is applied to said surface by pouring said concentrated liquid biocide composition onto said surface.

35. A method according to claim 33 wherein said concentrated liquid biocide composition is applied to said surface by spraying said concentrated liquid biocide composition onto said surface.

36. A method according to claim 33 wherein said concentrated liquid biocide composition is applied to said surface with an applicator.

37. A method according to claim 33 wherein said alkali metal dichlorohypobromite is a preformed aqueous solution of alkali metal dichlorohypobromite, and said aqueous solution of alkali metal salt of sulfamic acid is a preformed aqueous solution of the sodium salt of sulfamic acid.

38. A method according to claim 37 wherein said preformed aqueous solution of alkali metal dichlorohypobromite is a preformed aqueous solution of sodium dichlorohypobromite.

39. A method according to claim 33 wherein the pH of said composition is in the range of from 7 to about 13.5.

40. A method of sanitizing a body of water which comprises introducing into said body of water a concentrated liquid biocide composition formed from (a) alkali metal dichlorohypobromite and (b) an aqueous solution of alkali metal salt of sulfamic acid and alkali metal base, said solution having a pH of at least about 7, in amounts such that (i) the active bromine content of said composition is at least about 100,000 ppm (wt/wt), and (ii) the atom ratio of nitrogen to active bromine in said composition is greater than 1, and (iii) said composition has a pH of at least 7.

41. A method according to claim 40 wherein said concentrated liquid biocide composition is introduced directly into said body of water.

42. A method according to claim 40 wherein said concentrated liquid biocide composition is introduced into said body of water slowly over time.

43. A method according to claim 40 wherein said concentrated liquid biocide composition is introduced into said body of water via an apparatus through which the water is circulated.

44. A method according to claim 40 wherein the addition of said concentrated liquid biocide composition to said body of water yields in the range of from about 2 to about 10 milligrams per liter of total available halogen, expressed as $Cl_2$.

45. A method according to claim 44 wherein the total available halogen, expressed as $Cl_2$, is in the range of from about 2 to about 5 milligrams per liter.

46. A method according to claim 40 wherein the concentrated liquid biocide composition is introduced into said body of water as required, such that in the range of from about 2 to about 10 milligrams per liter of total available halogen, expressed as $Cl_2$, is maintained within said body of water.

47. A method according to claim 46 wherein the total available halogen, expressed as $Cl_2$, is in the range of from about 2 to about 5 milligrams per liter.

48. A method according to claim 40 wherein said alkali metal dichlorohypobromite is a preformed aqueous solution of alkali metal dichlorohypobromite, and said aqueous solution of alkali metal salt of sulfamic acid is a preformed aqueous solution of the sodium salt of sulfamic acid.

49. A method according to claim 48 wherein said preformed aqueous solution of alkali metal dichlorohypobromite is a preformed aqueous solution of sodium dichlorohypobromite.

50. A method according to claim 40 wherein the pH of said composition is in the range of from 7 to about 13.5.

* * * * *